United States Patent
Manabe

(10) Patent No.: US 11,865,746 B2
(45) Date of Patent: Jan. 9, 2024

(54) COMPOSITE SHEET MANUFACTURING DEVICE AND MANUFACTURING METHOD

(71) Applicant: ZUIKO CORPORATION, Settu (JP)

(72) Inventor: Takahito Manabe, Settu (JP)

(73) Assignee: ZUIKO CORPORATION, Settu (JP)

(*) Notice: Subject to any disclaimer, the term of this patent is extended or adjusted under 35 U.S.C. 154(b) by 221 days.

(21) Appl. No.: 16/649,822

(22) PCT Filed: Sep. 25, 2018

(86) PCT No.: PCT/JP2018/035514
§ 371 (c)(1),
(2) Date: Mar. 23, 2020

(87) PCT Pub. No.: WO2019/069751
PCT Pub. Date: Apr. 11, 2019

(65) Prior Publication Data
US 2020/0282608 A1     Sep. 10, 2020

(30) Foreign Application Priority Data

Oct. 6, 2017   (JP) .................................. 2017-195674

(51) Int. Cl.
*A61F 13/15*     (2006.01)
*A61F 13/511*    (2006.01)
(Continued)

(52) U.S. Cl.
CPC ........ *B29C 43/24* (2013.01); *A61F 13/15707* (2013.01); *A61F 13/15764* (2013.01);
(Continued)

(58) Field of Classification Search
CPC ................ A61F 13/15; A61F 13/15577; A61F 13/15699; A61F 13/15707;
(Continued)

(56) References Cited

U.S. PATENT DOCUMENTS

| | | | | |
|---|---|---|---|---|
| 4,280,978 A | * | 7/1981 | Dannheim | .............. B29C 51/22 |
| | | | | 264/156 |
| 7,323,072 B2 | * | 1/2008 | Engelhart | .............. D04H 1/542 |
| | | | | 156/73.2 |

(Continued)

FOREIGN PATENT DOCUMENTS

| JP | S34-000336 B1 | 1/1959 |
|---|---|---|
| JP | 2004-174234 A | 6/2004 |

(Continued)

OTHER PUBLICATIONS

PCT/ISA/210, "International Search Report for International Application No. PCT/JP2018/035514," dated Oct. 30, 2018.

(Continued)

*Primary Examiner* — Michael A Tolin
(74) *Attorney, Agent, or Firm* — Manabu Kanesaka

(57) ABSTRACT

In a composite sheet manufacturing device, a second roller having a plurality of first projections and a third roller are disposed so as to be adjacent to a first roller having multiple recessed areas. The outer diameters of the first and third rollers are the same size. The third roller is joined to the first roller with a first gear pair therebetween, so as to rotate at the same rotation frequency as that of the first roller. A first sheet that is fed in between the first roller and the second roller is shaped by being pushed into the recessed areas of the first roller by the first projections of the second roller. A second sheet is then superimposed onto the first sheet and is passed through the space between the first roller and the third roller, and the first and second sheets are thereby bonded to each other.

7 Claims, 8 Drawing Sheets

(51) Int. Cl.
*A61F 13/512* (2006.01)
*B32B 38/06* (2006.01)
*B29C 43/24* (2006.01)
*B29C 43/22* (2006.01)
*B29C 43/30* (2006.01)
*B29C 65/70* (2006.01)
*B29C 65/00* (2006.01)
*B29L 7/00* (2006.01)
*B29L 9/00* (2006.01)
*B32B 38/04* (2006.01)

(52) U.S. Cl.
CPC ........ *A61F 13/5123* (2013.01); *B29C 43/222* (2013.01); *B29C 43/305* (2013.01); *B29C 65/70* (2013.01); *B29C 66/7294* (2013.01); *A61F 2013/15715* (2013.01); *A61F 2013/15878* (2013.01); *A61F 2013/51182* (2013.01); *B29C 2793/0045* (2013.01); *B29L 2007/002* (2013.01); *B29L 2009/00* (2013.01); *B32B 2038/047* (2013.01); *B32B 2555/02* (2013.01)

(58) Field of Classification Search
CPC .......... A61F 13/15731; A61F 13/15764; A61F 13/51104; A61F 13/5116; A61F 13/512; A61F 13/5123; A61F 13/5125; A61F 2013/15715; A61F 2013/15821; A61F 2013/15861; A61F 2013/15878; A61F 2013/51178; A61F 2013/51182; B29C 43/222; B29C 43/24; B29C 43/305; B29C 59/002; B29C 59/02; B29C 59/04; B29C 65/70; B29C 66/729; B29C 66/7294; B29C 66/83413; B29C 2493/0045; B29C 2009/00; B29L 2007/002; B29L 2031/4878; B32B 3/266; B32B 3/28; B32B 3/30; B32B 5/022; B32B 5/26; B32B 5/265; B32B 5/266; B32B 37/0046; B32B 37/0053; B32B 37/0076; B32B 37/20; B32B 38/06; B32B 2038/047; B32B 2555/02

See application file for complete search history.

(56) References Cited

U.S. PATENT DOCUMENTS

| | | | |
|---|---|---|---|
| 9,186,280 B2* | 11/2015 | Umebayashi | ..... A61F 13/15731 |
| 2004/0140047 A1 | 7/2004 | Sato | |
| 2015/0290050 A1 | 10/2015 | Wada | |
| 2016/0235593 A1* | 8/2016 | Wada | ................ A61F 13/15739 |
| 2018/0140478 A1 | 5/2018 | Fukuhara | |

FOREIGN PATENT DOCUMENTS

| | | |
|---|---|---|
| JP | 2005-111908 A | 4/2005 |
| JP | 2006-175688 A | 7/2006 |
| WO | 2016/199543 A1 | 12/2016 |

OTHER PUBLICATIONS

Europe Patent Office, "Search Report for European Patent Application No. 18863864.7," dated Apr. 29, 2021.

* cited by examiner

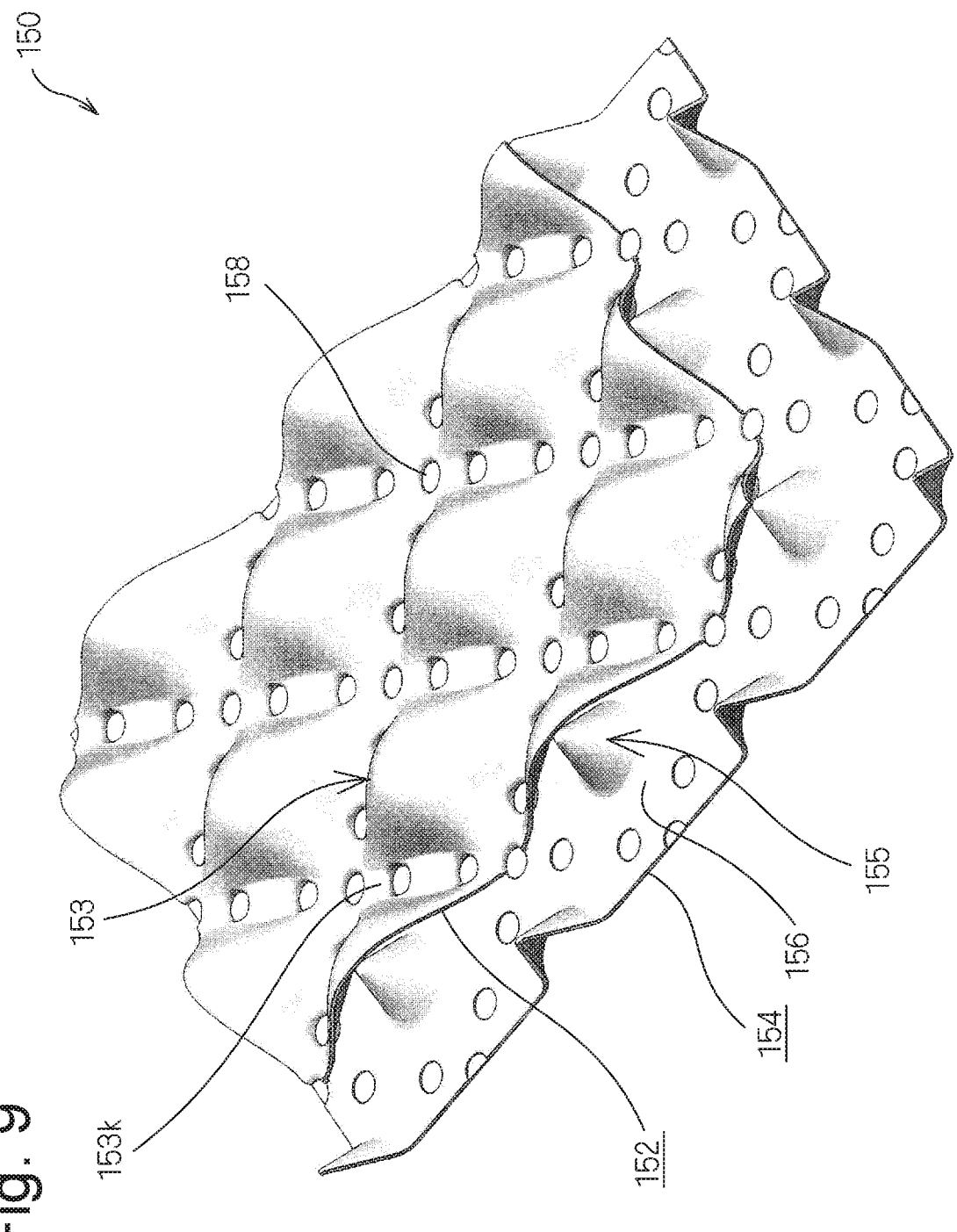

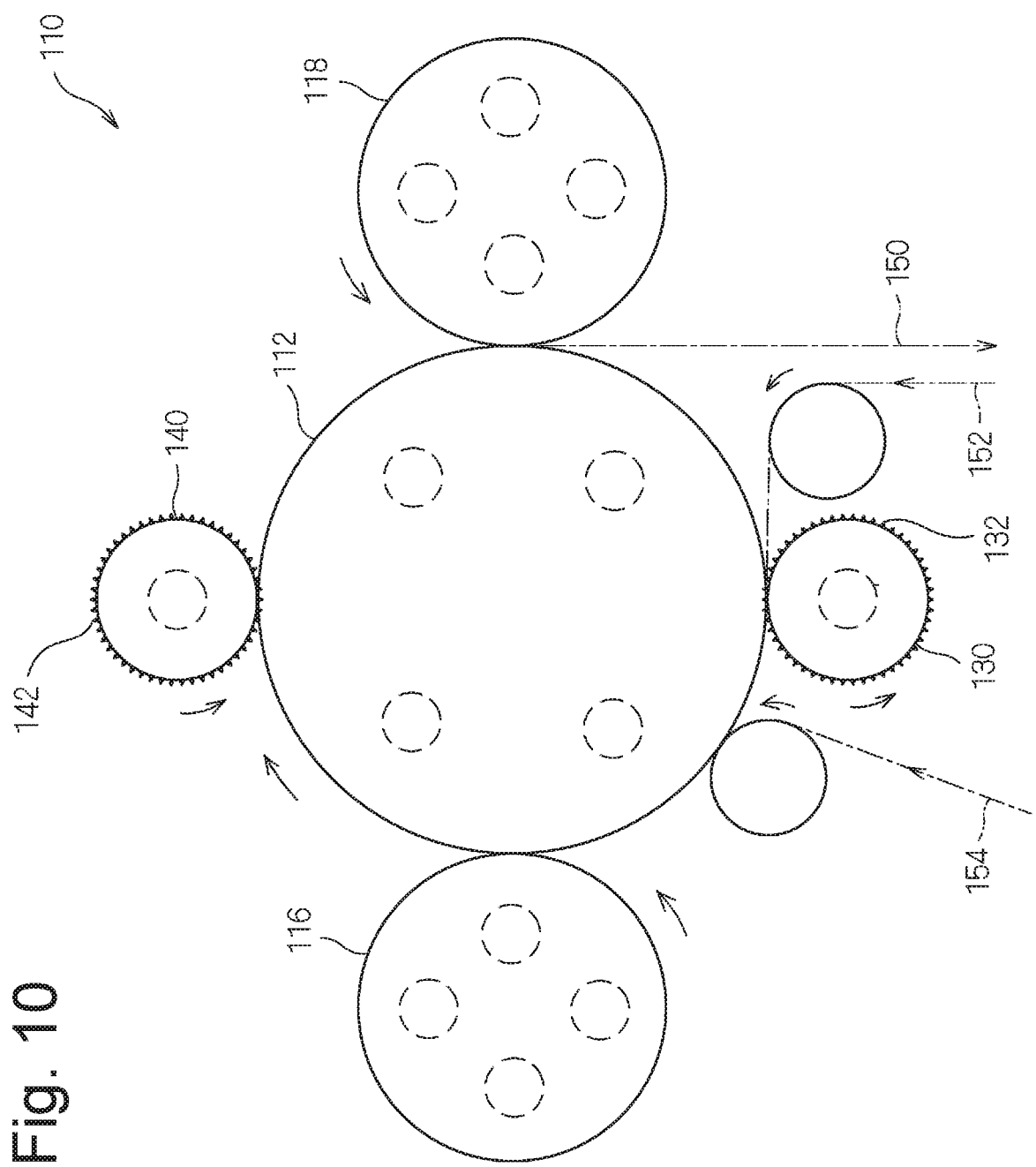

COMPOSITE SHEET MANUFACTURING DEVICE AND MANUFACTURING METHOD

RELATED APPLICATIONS

The present application is National Phase of International Application No. PCT/JP2018/035514 filed Sep. 25, 2018, and claim a priority from Japanese Application No. 2017-195674, filed Oct. 6, 2017, the disclosures of which are hereby incorporated by reference herein in its entirety.

TECHNICAL FIELD

The present invention relates to a composite sheet manufacturing device and manufacturing method, more particularly, to a device and method for manufacturing composite sheets having concave and convex shapes on the surfaces.

BACKGROUND ART

Composite sheets having concave and convex shapes on the surfaces thereof have been used for the skin-abutting faces of absorbent articles, such as disposable diapers and sanitary napkins. These kinds of composite sheets are manufactured by using such a device as shown in FIG. 7.

As shown in FIG. 7, in this device, a first sheet 84 is passed through the space between a first roller 81 having a circumferential face shaped into concave and convex shapes and a second roller 82 having a circumferential face shaped into convex and concave shapes to be engaged with the concave and convex shapes of the first roller 81, whereby the first sheet 84 is shaped into concave and convex shapes. A second sheet 85 is superimposed onto the first sheet 84 having been shaped into the concave and convex shapes, and the first sheets 84 and 85 are bonded by thermal fusion when they are passed through the space between the first roller 81 and a third roller 83, whereby a composite sheet 86 is completed (for example, refer to Patent Document 1).

Furthermore, for example, as shown in a sectional view in FIG. 8 and an image view in FIG. 9, a composite sheet 150 has been proposed in which both of a first sheet 152 and a second sheet 154 are shaped. As shown in FIGS. 8 and 9, the first sheet 152 has raised portions 153 shaped by shaping and boundary portions 153k adjacent to the raised portions 153. The second sheet 154 has projection portions 155 shaped by shaping and flat portions adjacent to the projection portions 155. The projection portions 155 protrude to the same side as the raised portions 153 of the first sheet 152 in the inside of the raised portions 153 of the first sheet 152. As shown in FIG. 9, in the boundary portions 153k of the first sheet 152, multiple bonded sections 158 in which the first sheet 152 and the second sheet 154 are bonded by thermal fusion, ultrasonic welding or adhesion using an adhesive are shaped at intervals, that is, intermittently.

The composite sheet 150 described above is manufactured using a device 110 shown in a schematic view in FIG. 10. As shown in FIG. 10, around a first roller 112 having multiple recessed areas, not shown, a second roller 130 having multiple first projections 132 to be inserted into and extracted from the recessed areas of the first roller 112 with a clearance therebetween, a third roller 116, a fourth roller 140, a fourth roller 140 having multiple second projections 142 to be inserted into and extracted from the recessed areas of the first roller 112 with a clearance therebetween and a fifth roller 118 are disposed in this device 110.

When being passed through the space between the first roller 112 and the second roller 130, the first sheet 152 is shaped, and the second sheet 154 is superimposed thereon. When being passed through the space between the first roller 112 and the third roller 116, both the superimposed sheets 152 and 154 are bonded to each other. Next, when being passed through the space between the first roller 112 and the fourth roller 140, the second sheet 154 is shaped. And then, both the superimposed sheets 152 and 154 are passed through the space between the first roller and the fifth roller 118, whereby the mutual bonding of both the sheets 152 and 154 is strengthened (for example, refer to Patent Document 2).

PRIOR ART DOCUMENT

Patent Document

Patent Document 1: JP-A-2005-111908
Patent Document 2: WO 2016/199543

SUMMARY OF INVENTION

Problem to be Solved by the Invention

When a composite sheet is manufactured, in the case that the rotation frequency of the first roller is made higher, the composite sheet can be manufactured at higher speed.

However, in the composite sheet manufacturing device in which the rollers 116, 118, 130 and 140 having outer diameters smaller than the outer diameter of the first roller 112 are disposed around the first roller 112 as shown in FIG. 10, it is not easy to make the rotation frequency of the first roller 112 higher; furthermore, if the rotation frequency of the first roller 112 is made higher, an unknown and new problem has been found in which the quality of the composite sheet becomes unstable.

In consideration of these circumstances, an object of the present invention is to provide a composite sheet manufacturing device and manufacturing method capable of manufacturing composite sheets easily at higher speed and capable of manufacturing composite sheets having stable quality even when the composite sheets are manufactured at higher speed.

Means for Solving the Problem

In order to solve the above-mentioned problem, the present invention provides a composite sheet manufacturing device configured as described below.

The composite sheet manufacturing device is equipped with (a) a first roller having a first outer circumferential face and a plurality of recessed areas retracted from the first outer circumferential face, (b) a second roller disposed so as to be adjacent to the first roller, rotated in synchronization with the first roller and having a second outer circumferential face opposed to the first outer circumferential face of the first roller and a plurality of first projections that protrude from the second outer circumferential face so as to be inserted into and extracted from the recessed areas of the first roller in a state in which a clearance is provided between each first projection thereof and each recessed area of the first roller, and (c) a third roller disposed so as to be adjacent to the first roller, rotated in synchronization with the first roller and having a third outer circumferential face opposed to the first outer circumferential face of the first roller. (i) A first sheet is fed in between the first roller and the second roller, conveyed while being supported by the first outer circumferential face of the first roller, and passed through a space between the first roller and the second roller, (ii) when the first sheet is passed through the space between the first roller and the second roller, the first projections of the second roller push the first sheet into the recessed areas of the first roller, and thereby the first sheet is shaped, (iii) a second sheet is superimposed onto the shaped first sheet and conveyed together with the first sheet and then passed through a space between the first roller and the third roller, and (iv) when the first sheet and the second sheet are passed through the space between the first roller and the third roller, the first roller and the third roller hold the first sheet and the second sheet therebetween, and thereby the first sheet and the second sheet are bonded to each other. (A) Each outer diameter of the first roller and the third roller is the same size, and (B) the third roller is joined to the first roller with a first gear pair therebetween so as to rotate at the same rotation frequency as that of the first roller.

With the above-mentioned configuration, since the first and third rollers are rotated at the same rotation frequency, the rotation frequency of the first roller is made higher easily in comparison with the configuration in which the rotation frequency of the third roller is higher than the rotation frequency of the first roller. As the rotation frequency of the first roller is made higher, the composite sheet can be manufactured at higher speed.

Hence, the composite sheet is manufactured easily at higher speed.

Furthermore, since the first roller and the third roller are joined mutually via the gears, the relative rotation error between the first roller and the third roller is unchanged even when the rotation frequency is changed. Hence, the quality of the composite sheet can be maintained even when the rotation frequency of the first roller is made higher.

Moreover, since the first roller and the third roller that hold the first and second sheets therebetween so as to bond the sheets are equal in outer diameter, rotate at the same rotation frequency and are always opposed mutually at the same portions, the rollers fit easily. Hence, the satisfactory bonding state between the first sheet and the second sheet can be maintained.

Still further, since the outer diameters of the first and third rollers are the same size and since the first roller is opposed mutually to the third roller at the same portion at all times, readjustment at the time of component exchange is made easy, and assembling accuracy is maintained easily. As a result, the quality of the manufactured composite sheet can be maintained constant.

Hence, even when the composite sheet is manufactured at higher speed, it is possible to manufacture the composite sheet having stable quality.

Preferably, an outer diameter of the second roller is equal to the outer diameters of the first roller and the second roller. The second roller is joined to the first roller with a second gear pair therebetween so as to rotate at the same rotation frequency as that of the first roller.

In this case, since the first roller and the second roller are joined mutually via the second gear pair, the relative rotation error between the first roller and the second roller is unchanged even when the rotation frequency is changed. Moreover, each of the recessed areas of the first roller corresponds one-to-one to each of the first projections of the second roller, while the first projections are inserted into and extracted from the recessed areas. Hence, the satisfactorily shaped state of the first sheet can be maintained.

Still further, since the outer diameters of the first and the second roller are the same size and since the first roller is opposed mutually to the second roller at the same portion at all times, readjustment at the time of component exchange is made easy, and assembling accuracy is maintained easily. As a result, the quality of the manufactured composite sheet can be maintained constant.

Hence, the composite sheet having more stable quality can be manufactured.

In a preferred embodiment, the composite sheet manufacturing device is further equipped with (d) a fourth roller disposed so as to be adjacent to the first roller, rotated in synchronization with the first roller and having a fourth outer circumferential face opposed to the first outer circumferential face of the first roller and a plurality of second projections that protrude from the fourth outer circumferential face so as to be inserted into and extracted from the recessed areas of the first roller in a state in which a clearance is provided between each second projection thereof and each recessed area of the first roller and (e) a fifth roller disposed so as to be adjacent to the first roller, rotated in synchronization with the first roller and having a fifth outer circumferential face opposed to the first outer circumferential face. (v) The first sheet and the second sheet having been passed through the space between the first roller and the third roller and bonded to each other are conveyed while being supported by the first outer circumferential face of the first roller and are passed through a space between the first roller and the fourth roller and then passed through a space between the first roller and the fifth roller, (vi) when the first sheet and the second sheet are passed through the space between the first roller and the fourth roller, the second projections of the fourth roller push the second sheet into the recessed areas of the first roller, and thereby the second sheet is shaped, (vii) when the first sheet and the second sheet are passed through the space between the first roller and the fifth roller, the first roller and the fifth roller hold the first sheet and the second sheet therebetween, and thereby the mutual bonding of the first sheet and the second sheet is strengthened. (C) An outer diameter of the fifth roller is equal to each outer diameter of the first roller and the third roller, and (D) the fifth roller is joined to the first roller with a third gear pair therebetween so as to rotate at the same rotation frequency as that of the first roller.

In this case, a composite sheet in which both of the first sheet and the second sheet thereof are formed is manufactured easily at higher speed. Furthermore, even when the composite sheet is manufactured at higher speed, it is possible to manufacture the composite sheet having stable quality.

Preferably, an outer diameter of the fourth roller is equal to each outer diameters of the first roller and the third roller. The fourth roller is joined to the first roller with a fourth gear pair therebetween so as to rotate at the same rotation frequency as that of the first roller.

In this case, since the first roller and the fourth roller are joined mutually via the fourth gear pair, the relative rotation error between the first roller and the fourth roller is unchanged even when the rotation frequency is changed. Moreover, each of the recessed areas of the first roller corresponds one-to-one to each of the second projections of the fourth roller, while the second projections are inserted into and extracted from the recessed areas. Hence, the satisfactorily shaped state of the second sheet can be maintained.

Still further, since the outer diameters of the first and the fourth roller are the same size and since the first roller is opposed mutually to the fourth roller at the same portion at all times, readjustment at the time of component exchange is made easy, and assembling accuracy is maintained easily. As a result, the quality of the manufactured composite sheet can be maintained constant.

Hence, the composite sheet having further more stable quality can be manufactured.

Moreover, in order to solve the above-mentioned problem, the present invention provides a composite sheet manufacturing method configured as described below.

A composite sheet manufacturing method has (i) a first step of disposing a second roller having first projections and a third roller so as to be adjacent to a first roller having a plurality of recessed areas retracted from an outer circumferential face of the first roller, rotating the first roller, the second roller and the third roller in synchronization with one another, and making the first projections of the second roller to be inserted into or extracted from the recessed areas of the first roller in a state in which a clearance is provided between each first projection of the second roller and each recessed area of the first roller, (ii) a second step of feeding a first sheet in between the first roller and the second roller being rotated, conveying the first sheet while supporting the first sheet on the outer circumferential face of the first roller, making the first sheet to be passed through a space between the first roller and the second roller, and making the first sheet to be pushed into the recessed areas of the first roller by the first projections of the second roller when the first sheet is passed through the space between the first roller and the second roller, thereby shaping the first sheet, (iii) a third step of superimposing a second sheet onto the shaped first sheet, conveying the second sheet together with the first sheet, and making the first sheet and the second sheet to be passed through a space between the first roller and the third roller, and holding the first sheet and the second sheet between the first roller and the third roller when the first sheet and the second sheet are passed through the space between the first roller and the third roller, thereby bonding the first sheet and the second sheet to each other. At the first step, (A) each outer diameter of the first roller and the third roller is made the same size, and (B) the third roller is joined to the first roller with a first gear pair therebetween, and the third roller is made to rotate at the same rotation frequency as that of the first roller.

With the above-mentioned method, since the first and third rollers are rotated at the same rotation frequency, the rotation frequency of the first roller can be made higher easily in comparison with the case in which the rotation frequency of the third roller is higher than the rotation frequency of the first roller. As the rotation frequency of the first roller is made higher, the composite sheet can be manufactured at higher speed.

Hence, the composite sheet can be manufactured easily at higher speed.

Furthermore, according to the above-mentioned method, since the first roller and the third roller are joined mutually via the gears, the relative rotation error between the first roller and the third roller is unchanged even when the rotation frequency is changed. Hence, the quality of the composite sheet can be maintained even when the rotation frequency of the first roller is made higher.

Moreover, since the first roller and the third roller that hold the first and second sheets therebetween so as to bond the sheets are equal in outer diameter, rotate at the same rotation frequency, and are always opposed mutually at the same portions, the rollers fit easily. Hence, the satisfactory bonding state between the first sheet and the second sheet can be maintained.

Still further, since the outer diameters of the first and third rollers are the same size and since the rollers are mutually opposed to each other at the same portions at all times, readjustment at the time of component exchange is made easy, and assembling accuracy is maintained easily. As a result, the quality of the manufactured composite sheet can be maintained constant.

Hence, even when the composite sheet is manufactured at higher speed, it is possible to manufacture the composite sheet having stable quality.

Preferably, at the first step, an outer diameter of the second roller is made equal to each outer diameter of the first roller and the third roller, the second roller is joined to the first roller with a second gear pair therebetween, and the second roller is made to rotate at the same rotation frequency as that of the first roller.

In this case, since the first roller and the second roller are joined mutually via the second gear pair, the relative rotation error between the first roller and the second roller is unchanged even when the rotation frequency is changed. Moreover, each of the recessed areas of the first roller corresponds one-to-one to each of the first projections of the second roller, while the first projections are inserted into and extracted from the recessed areas. Hence, the satisfactorily shaped state of the first sheet can be maintained.

Still further, since the outer diameters of the first and the second roller are the same size and since the first roller is opposed mutually to the second roller at the same portion at all times, readjustment at the time of component exchange is made easy, and assembling accuracy is maintained easily. As a result, the quality of the manufactured composite sheet can be maintained constant.

Hence, the composite sheet having more stable quality can be manufactured.

In a preferred embodiment, the composite sheet manufacturing method further has (iv) a fourth step of disposing a fourth roller having a plurality of second projections and a fifth roller so as to be adjacent to the first roller, rotating the fourth roller and the fifth roller in synchronization with the first roller, and making the second projections of the fourth roller to be inserted into or extracted from the recessed areas of the first roller in a state in which a clearance is provided between each second projection of the fourth roller and each recessed area of the first roller, (v) a fifth step of conveying the first sheet and the second sheet having been passed through the space between the first roller and the third roller and bonded to each other while supporting the first sheet and the second sheet on the outer circumferential face of the first roller, making the first sheet and the second sheet to be passed through a space between the first roller and the fourth roller, and then making the first sheet and the second sheet to be passed through a space between the first roller and the fifth roller, (vi) a sixth step of pushing the second sheet into the recessed areas of the first roller by the second projections of the fourth roller when the first sheet and the second sheet are passed through the space between the first roller and the fourth roller, thereby shaping the second sheet, and (vii) a seventh step of holding the first sheet and the second sheet between the first roller and the fifth roller when the first sheet and the second sheet are passed through the space between the first roller and the fifth roller, thereby strengthening the mutual bonding of the first sheet and the second sheet. At the fourth step, (C) an outer diameter of the fifth roller is made equal to each outer diameter of the first roller and the third roller, and (D) the fifth roller is joined to the first roller with a third gear pair therebetween, and the fifth roller is made to rotate at the same rotation frequency as that of the first roller.

In this case, a composite sheet in which both of the first sheet and the second sheet thereof are formed is manufactured easily at higher speed. Furthermore, even when the composite sheet is manufactured at higher speed, it is possible to manufacture the composite sheet having stable quality.

Preferably, at the fourth step, the outer diameter of the fourth roller is made equal to each outer diameter of the first roller and the third roller, the fourth roller is joined to the first roller with a fourth gear pair therebetween, and the fourth roller is made to rotate at the same rotation frequency as that of the first roller.

In this case, since the first roller and the fourth roller are joined mutually via the gears, the relative rotation error between the first roller and the fourth roller is unchanged even when the rotation frequency is changed. Moreover, each of the recessed areas of the first roller corresponds one-to-one to each of the second projections of the fourth roller, the projections being inserted into and extracted from the recessed areas. Hence, the satisfactorily shaped state of the second sheet can be maintained.

Still further, since the outer diameters of the first and the fourth roller are the same size and since the first roller is opposed mutually to the fourth roller at the same portion at all times, readjustment at the time of component exchange is made easy, and assembling accuracy is maintained easily. As a result, the quality of the manufactured composite sheet can be maintained constant.

Hence, the composite sheet having further more stable quality can be manufactured.

Effects of Invention

According to the present invention, the composite sheet can be manufactured easily at higher speed, and even when the composite sheet is manufactured at higher speed, the composite sheet having stable quality can be manufactured.

BRIEF DESCRIPTION OF DRAWINGS

FIG. 9 is an image view of the composite sheet (Conventional Example 2); and

FIG. 10 is a schematic view showing a composite sheet manufacturing device (Conventional Example 2).

MODE FOR CARRYING OUT THE INVENTION

Figure 1:
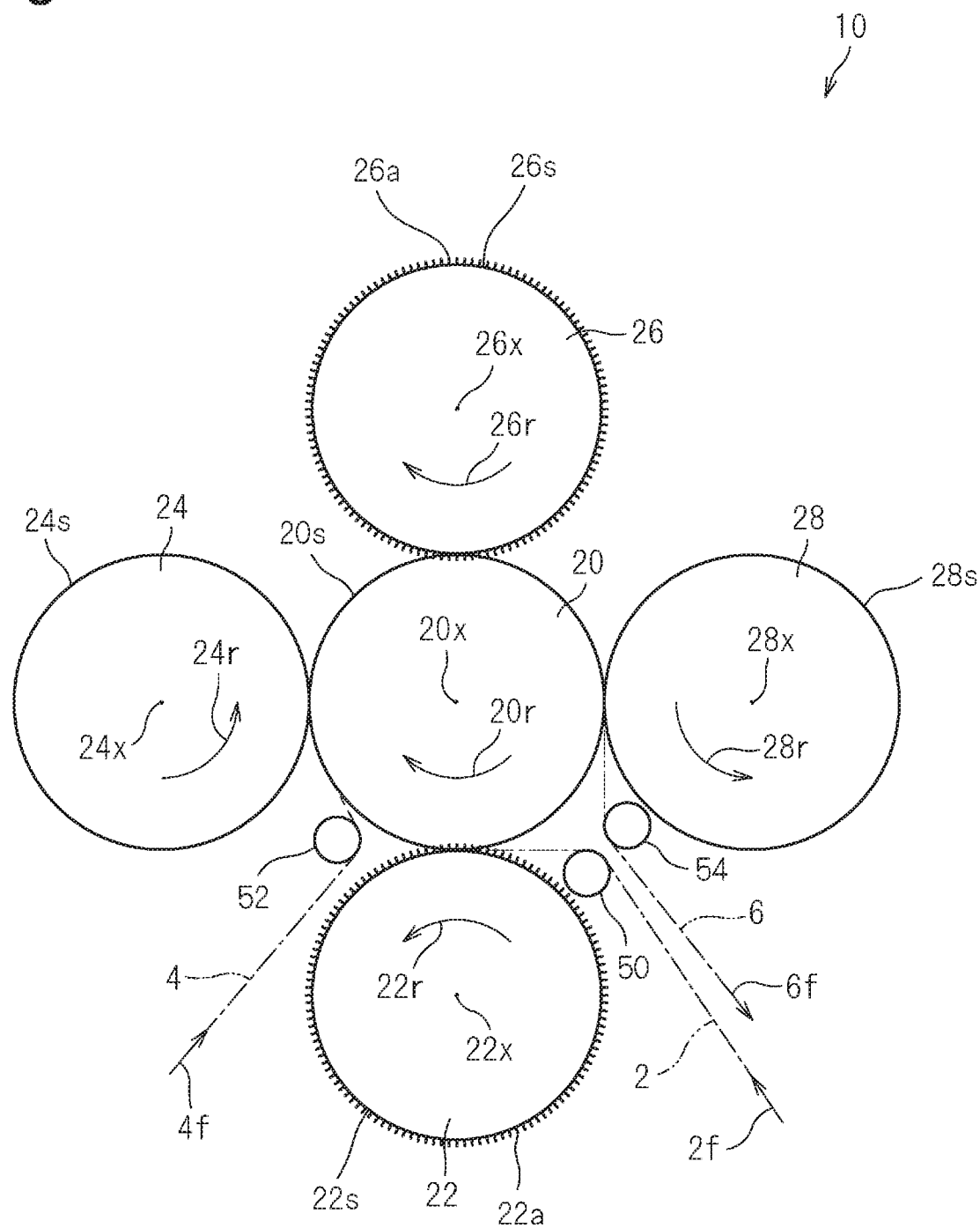
FIG. 1 is a schematic view showing a composite sheet manufacturing device (Embodiment 1)

Embodiments according to the present invention will be described below referring to the drawings.

Embodiment 1

A composite sheet manufacturing device and a composite sheet manufacturing method according to Embodiment 1 will be described referring to FIGS. 1 to 4.

FIG. 1 is a schematic view showing a configuration of a composite sheet manufacturing device 10. As shown in FIG. 1, in the composite sheet manufacturing device 10, second to fifth rollers 22, 24, 26 and 28 are disposed in this order so as to be adjacent to a first roller 20. The rotation center lines 20$x$, 22$x$, 24$x$, 26$x$ and 28$x$ of the first to fifth rollers 20, 22, 24, 26 and 28 are parallel to one another, and the first to fifth rollers 20, 22, 24, 26 and 28 rotate in the directions indicated by arrows 20$r$, 22$r$, 24$r$, 26$r$ and 28$r$, respectively, in synchronization with one another.

Although the second to fifth rollers 22, 24, 26 and 28 can be disposed at appropriate intervals around the first roller 20, in the case that they are disposed uniformly as shown in FIG. 1, the first to fifth rollers 20, 22, 24, 26 and 28 can easily perform high-speed rotation.

Figure 4:
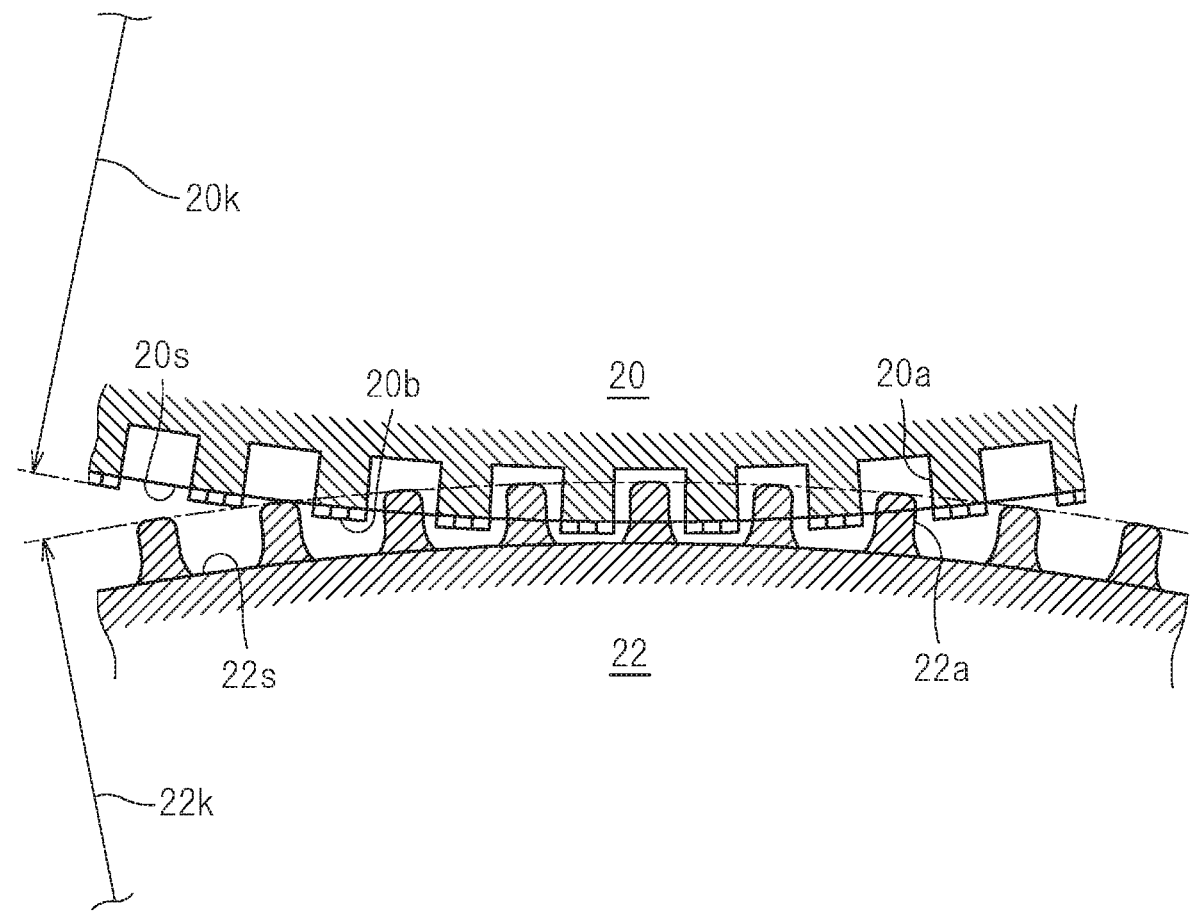
FIG. 4 is an enlarged sectional view showing the main part of the composite sheet manufacturing device (Embodiment 1)

FIG. 4 is an enlarged sectional view showing the main part of the composite sheet manufacturing device 10. As shown in FIG. 4, the first roller 20 has a first outer circumferential face 20$s$ having a cylindrical shape, multiple recessed areas 20$a$ retracted inward in the radial direction from the first outer circumferential face 20$s$ and multiple seal projections 20$b$ protruding outward in the radial direction from the outer circumferential face 20$s$.

The second roller 22 has a second outer circumferential face 22$s$ having a cylindrical shape and being opposed to the first outer circumferential face 20$s$ of the first roller 20 and first projections 22$a$ that are inserted into and extracted from the recessed areas 20$a$ of the first roller 20 in a state in which a clearance is provided between each projection thereof and each recessed area 20$a$ of the first roller 20.

As shown in FIG. 1, the third roller 24 has a third outer circumferential face 24$s$ having a cylindrical shape and being opposed to the first outer circumferential face 20$s$ of the first roller 20.

Like the second roller 22, the fourth roller 26 has a fourth outer circumferential face 26$s$ having a cylindrical shape and being opposed to the first outer circumferential face 20$s$ of the first roller 20 and second projections 26$a$ that are inserted into and extracted from the recessed areas 20$a$ of the first roller 20 in a state in which a clearance is provided between each projection thereof and each recessed area 20$a$ (see FIG. 4) of the first roller 20. The second projections 26$a$ are preferably smaller than the first projections 22$a$ of the second roller 22 in height and width.

Like the third roller 24, the fifth roller 28 has a fifth outer circumferential face 28$s$ having a cylindrical shape and being opposed to the first outer circumferential face 20$s$ of the first roller 20.

The outer diameters of the first to fifth rollers 20, 22, 24, 26 and 28 are the same size. The outer diameter of the first roller 20 is twice as large as the radius 20$k$ (see FIG. 4) ranging from the rotation center line 20$x$ of the first roller 20 to the tip of the seal projection 20$b$ (see FIG. 4) of the first roller 20. The outer diameter of the second roller 22 is twice as large as the radius 22$k$ (see FIG. 4) ranging from the rotation center line 22$x$ of the second roller 22 to the tip of the first projection 22$a$ of the second roller 22. The outer diameter of the third roller 24 is the diameter of the third outer circumferential face 24s of the third roller 24. The outer diameter of the fourth roller 26 is twice as large as the radius ranging from the rotation center line 26x of the fourth roller 26 to the tip of the second projection 26a (see FIG. 4) of the fourth roller 26. The outer diameter of the fifth roller 28 is the diameter of the fifth outer circumferential face 28s of the fifth roller 28.

Figure 2:
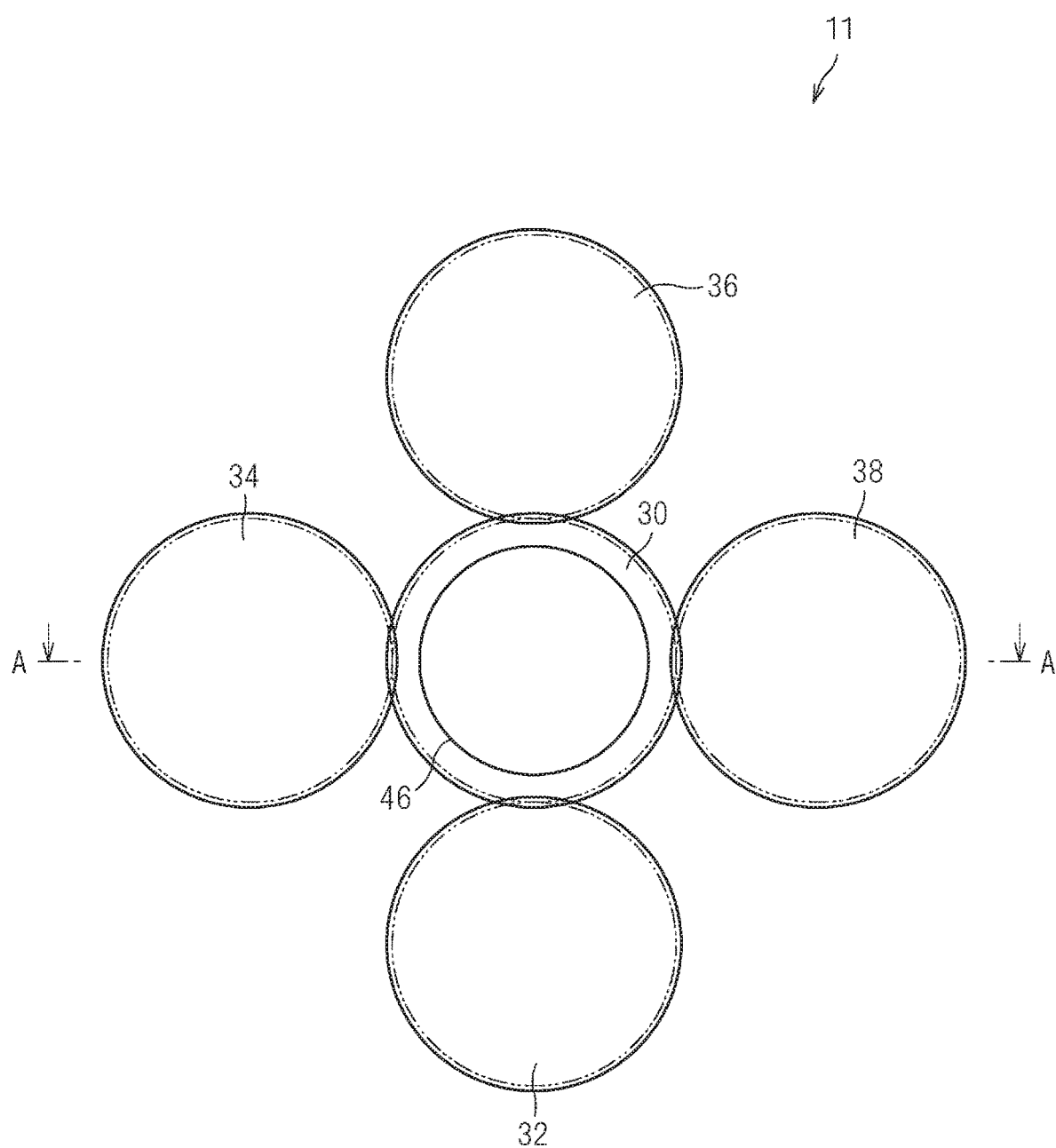
FIG. 2 is a schematic view showing the drive mechanism of the composite sheet manufacturing device (Embodiment 1)

FIG. 2 is a schematic view showing the drive mechanism 11 of the composite sheet manufacturing device 10, viewed in parallel to the rotation center lines 20x, 22x, 24x, 26x and 28x (see FIG. 1). As shown in FIG. 2, in the drive mechanism 11, second to fifth gears 32, 34, 36 and 38 are disposed around a first gear 30 so as to be engaged with the first gear 30. The mechanism is configured so that the rotations of the first to fifth gears 30, 32, 34, 36 and 38 are transmitted to the first to fifth rollers 20, 22, 24, 26 and 28, respectively. The mechanism may be configured so that multiple first gears 30 are provided and so that one of the second to fifth rollers 22, 24, 26 and 28 is engaged with one of the first gears and another one of the second to fifth rollers 22, 24, 26 and 28 is engaged with another one of the first gears.

Figure 3:
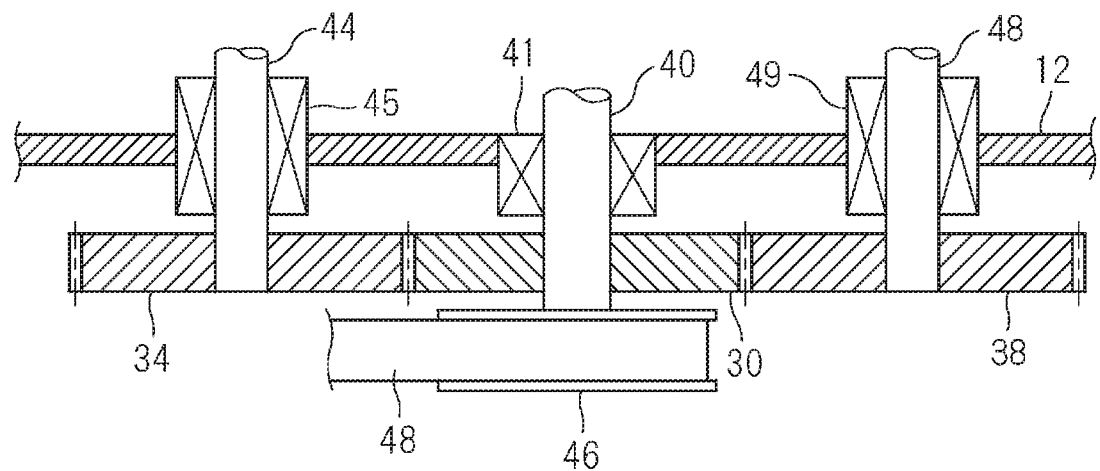
FIG. 3 is a sectional view taken on line A-A of FIG. 2 (Embodiment 1)

FIG. 3 is a sectional view taken on line A-A of FIG. 2. As shown in FIG. 3, the first gear 30 is fixed to a first rotation shaft 40 that is rotatably supported by the frame 12 of the composite sheet manufacturing device 10 via a bearing 41. The first rotation shaft 40 is joined to the first roller 20 via a shaft joint, not shown, whereby the rotation of the first gear 30 is transmitted to the first roller 20 and the first roller 20 rotates at the same rotation frequency as that of the first gear 30.

Similarly, the second to fifth gears 32, 34, 36 and 38 are fixed to second to fifth rotation shafts 42, 44, 46 and 48 (42 and 46 are not shown) that are rotatably supported by the frame 12 of the composite sheet manufacturing device 10 via bearings 43, 45, 47 and 48 (43 and 47 are not shown), respectively. The second to fifth rotation shafts 42, 44, 46 and 48 are joined to the second to fifth rollers 20, 22, 24, 26 and 28, respectively, via shaft joints, not shown, whereby the second to fifth rollers 20, 22, 24, 26 and 28 rotate at the same rotation frequency as that of the gears 32, 34, 36 and 38. In other words, the third roller 24 is joined to the first roller 20 with a first gear pair composed of the gears 30 and 34 so that the third roller 24 rotates at the same rotation frequency as that of the first roller 20. The second roller 22 is joined to the first roller 20 with a second gear pair composed of the gears 30 and 32 so that the second roller 22 rotates at the same rotation frequency as that of the first roller 20. The fifth roller 28 is joined to the first roller 20 with a third gear pair composed of the gears 30 and 38 so that the fifth roller 28 rotates at the same rotation frequency as that of the first roller 20. The fourth roller 26 is joined to the first roller 20 with a fourth gear pair composed of the gears 30 and 36 so that the fourth roller 26 rotates at the same rotation frequency as that of the first roller 20.

The first to fifth gears 30, 32, 34, 36 and 38 may be joined to the first to fifth rollers 20, 22, 24, 26 and 28, respectively, with reduction mechanisms having the same reduction ratio or speed increasing mechanisms having the same speed increasing ratio.

As shown in FIG. 3, a pulley 46 is fixed to the first rotation shaft 40. The rotation of a drive motor, not shown, is transmitted to the pulley 46 via a timing belt 48.

The numbers of the teeth of the gears 30, 32, 34, 36 and 38 are the same, and the first gear 30 is engaged with the second to fifth gears 32, 34, 36 and 38. Hence, when the rotation is transmitted to the pulley 46 via the drive motor, not shown, the first gear 30 is rotated, and the second to fifth gears 32, 34, 36 and 38 are rotated at the same rotation frequency as that of the first gear 30, whereby the first to fifth rollers 20, 22, 24, 26 and 28 are rotated at the same rotation frequency.

Although a good balance is attained in the case that the rotation of the drive motor is distributed from the first rotation shaft 40 to the other rotation shafts 42, 44, 46 and 48, it is possible that the rotation of the drive motor is transmitted to one or two or more of the rotation shafts 42, 44, 46 and 48 other than the first rotation shaft 40 and that the rotation of the rotation shaft is distributed to the other rotation shafts.

Figure 8:
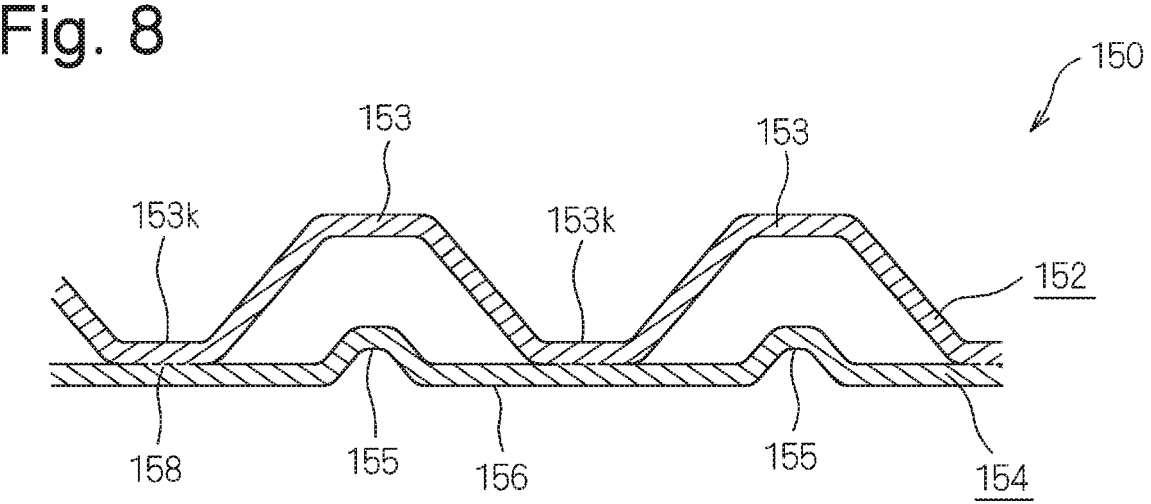
FIG. 8 is a sectional view showing a composite sheet (Conventional Example 2)

As shown in FIG. 1, in the composite sheet manufacturing device 10, a first sheet 2 and a second sheet 4 are fed, and a composite sheet 6 is manufactured and ejected. The composite sheet 6 has a configuration similar to that of the composite sheet 150 shown in FIGS. 8 and 9, wherein both the first sheet 2 and the second sheet 4 are shaped and the first sheet 2 and the second sheet 4 are bonded intermittently. Although appropriate materials may merely be selected as the materials of the first sheet 2 and the second sheet 4, materials that are deformed and fused when heated, for example, nonwoven fabrics containing resin material, are preferably used.

As indicated by an arrow 2f, the first sheet 2 is fed in between the first roller 20 and the second roller 22 via a first guide roller 50. The first sheet 2 is supported by the outer circumferential face 20s of the first roller 20 and conveyed in synchronization with the rotation of the first roller 20.

As indicated by an arrow 4f, the second sheet 4 is superimposed onto the first sheet 2 via a second guide roll 52 and conveyed together with the first sheet 2.

The superimposed first sheet 2 and second sheet 4 are passed through the space between the first roller 20 and the third roller 24, the space between the first roller 20 and the fourth roller 26 and the space between the first roller 20 and the fifth roller 28 in this order, whereby the completed composite sheet 6 is ejected via a third guide roller 54 as indicated by an arrow 6f.

When the first sheet 2 is passed through the space between the first roller 20 and the second roller 22, the first sheet 2 is shaped by being pushed into the recessed areas 20a of the first roller 20 by the first projections 22a of the second roller 22, thereby being shaped into a predetermined shape.

In the case of a configuration in which the first sheet 2 is held between the first outer circumferential face 20s of the first roller 20 and the second outer circumferential face 22s of the second roller 22 when the first sheet 2 is passed through the space between the first roller 20 and the second roller 22, the first sheet 2 can be shaped easily, whereby this configuration is preferable. However, even in the case of a configuration in which the first sheet 2 is passed through between the first outer circumferential face 20s of the first roller 20 and the second outer circumferential face 22s of the second roller 22 with a clearance provided therebetween, it is possible to shape the first sheet 2.

The first roller 20 is preferably configured so as to suction-hold the first sheet 2. For example, the first outer circumferential face 20s and the recessed areas 20a (see FIG. 4) of the first roller 20 are provided with air suction holes, not shown.

When the second sheet 4 is passed through the space between the first roller 20 and the fourth roller 26, the second sheet 4 is shaped by being pushed into the recessed areas 20a (see FIG. 4) of the first roller 20 by the second projections 26a of the fourth roller 26, thereby being shaped into a predetermined shape.

The tips of the second projections 26a of the fourth roller 26 may be sharpened, and through holes may be formed in the shaped portions of the second sheet 4 using the second projections 26a of the fourth roller 26.

A heater, not shown, is provided in the inside of each of the first roller 20, the third roller 24 and the fifth roller 28. Hence, when the first sheet 2 and the second sheet 4 are held between the seal projections 20b (see FIG. 4) of the first roller 20 and the outer circumferential face 24s of the third roller 24, the first sheet 2 and the second sheet 4 are bonded to each other by thermal fusion. Furthermore, when the first sheet 2 and the second sheet 4 having been bonded to each other are held between the seal projections 20b (see FIG. 4) of the first roller 20 and the outer circumferential face 28s of the fifth roller 28, the mutual bonding is strengthened.

The heater can be provided only in the first roller 20, or the heater can be provided in only each of the third roller 24 and the fifth roller 28. Furthermore, at least one of the first roller 20, the third roller 24 and the fifth roller 28 can be heated by a heating means, such as a heater, provided outside.

The region where the first sheet 2 and the second sheet 4 make contact with each other can be bonded intermittently by providing the multiple seal projections 20b (see FIG. 4) on the outer circumferential face 20s of the first roller 20. However, the entire region where the first sheet 2 and the second sheet 4 make contact with each other can be bonded continuously by eliminating the seal projections 20b (see FIG. 4) and by holding the first sheet 2 and the second sheet 4 between the first outer circumferential face 20s of the first roller 20 and the third outer circumferential face 24s of the third roller 24.

Next, processing for manufacturing the composite sheet 6 using the composite sheet manufacturing device 10 will be described.

(1-1) First, the second roller 22 having the first projections 22a and the third roller 24 are disposed so as to be adjacent to the first roller 20 having the multiple recessed areas 20a formed on the outer circumferential face 20s thereof, the first roller 20, the second roller 22 and the third roller 24 are rotated in synchronization with one another, and the first projections 22a of the second roller 22 are inserted into and extracted from the recessed areas 20a of the first roller 20 in a state in which a clearance is provided between each projection thereof and each recessed area 20a of the first roller 20. The outer diameters of the first roller 20 and the third roller 24 are made equal, and the third roller 24 is joined to the first roller 20 with the first gear pair composed of the gears 30 and 34, whereby the third roller 24 is rotated at the same rotation frequency as that of the first roller 20. Moreover, the outer diameter of the second roller 22 is made equal to the outer diameters of the first roller 20 and the third roller 24, and the second roller 22 is joined with the second gear pair composed of the gears 30 and 32, whereby the second roller 22 is rotated at the same rotation frequency as that of the first roller 20. The processing up to this step is a first step.

(1-2) Furthermore, the fourth roller 26 having the second projection 26a and the fifth roller 28 are disposed so as to be adjacent to the first roller 20, the fourth roller 26 and the fifth roller 28 are rotated in synchronization with the first roller 20, and the projections 26b of the fourth roller 26 are inserted into and extracted from the recessed areas 20a of the first projections 22a in a state in which a clearance is provided between each projection thereof and each recessed area 20a of the first roller 20. The outer diameter of the fifth roller 28 is made equal to the outer diameters of the first roller 20 and the third roller 24, and the fifth roller 28 is joined to the first roller 20 with the third gear pair composed of the gears 30 and 38, whereby the fifth roller 28 is rotated at the same rotation frequency as that of the first roller 20. Moreover, the outer diameter of the fourth roller 26 is made equal to the respective outer diameters of the first roller 20 and the third roller 24, and the fourth roller 26 is joined to the first roller 20 with the fourth gear pair composed of the gears 30 and 36, whereby the fourth roller 26 is rotated at the same rotation frequency as that of the first roller 20. The processing up to this step is a fourth step.

(2) Next, the first sheet 2 is fed in between the first roller 20 and the second roller 22 that are rotating, conveyed while being supported by the outer circumferential face 20s of the first roller 20, and then passed through the space between the first roller 20 and the third roller 24. When the first sheet 2 is passed through the space between the first roller 20 and the third roller 24, the first sheet 2 is shaped by being pushed into the recessed areas 20a of the first roller 20 by the first projections 22a of the second roller 22. The processing up to this step is a second step.

(3) Next, the second sheet 4 is superimposed onto the first sheet 2 having been shaped, conveyed together with the first sheet 2, and passed through the space between the first roller 20 and the third roller 24. When the first sheet 2 and the second sheet 4 are passed through the space between the first roller 20 and the third roller 24, the first sheet 2 and the second sheet 4 are held between the first roller 20 and the third roller 24, whereby the first sheet 2 and the second sheet 4 are bonded to each other. The processing up to this step is a third step.

(4) Next, the first sheet 2 and the second sheet 4 having been passed through the space between the first roller 20 and the third roller 24 and bonded to each other are conveyed while being supported by the outer circumferential face 20s of the first roller 20, are passed through the space between the first roller 20 and the fourth roller 26, and then passed through the space between the first roller 20 and the fifth roller 28. The processing up to this step is a fifth step.

(5) Next, when the first sheet 2 and the second sheet 4 are being passed through the space between the first roller 20 and the fourth roller 26, the second sheet 4 is shaped by being pushed into the recessed areas 20a of the first roller 20 by the second projections 26a of the fourth roller 26. The processing up to this step is a sixth step.

(6) Next, when the first sheet 2 and the second sheet 4 are passed through the space between the first roller 20 and the fifth roller 28, the first sheet 2 and the second sheet 4 are held between the first roller 20 and the fifth roller 28, whereby the mutual bonding of the first sheet 2 and the second sheet 4 is strengthened. The processing up to this step is a seventh step.

When the composite sheet 6 is manufactured by performing the above-mentioned steps, raised portions shaped by the first projections 22a of the second roller 22 are formed at the positions corresponding to the recessed areas 20a of the first roller 20. Furthermore, bonded sections wherein the first sheet 2 and the second sheet 4 are bonded to each other are formed at the positions corresponding to the seal projections 20b of the first roller 20. For example, the bonded sections are disposed in a scattered state around the raised portions. The portions in which the second sheet 4 is shaped by the second projection 26a of the fourth roller 26 are disposed inside the raised portions of the first sheet 2.

As described above, in the composite sheet manufacturing device 10, the first to fifth rollers 20, 22, 24, 26 and 28 being equal in outer diameter are joined to one another via the gears 30, 32, 34, 36 and 38 and are rotated at the same rotation frequency. The composite sheet 6 can be manufactured easily at higher speed and the composite sheet 6 having stable quality can be maintained even when the composite sheet 6 is manufactured at higher speed by using the composite sheet manufacturing device 10.

More specifically, when the rotation frequency of the rollers become higher, problems such as the heat generation of the bearings and the vibration of the rollers will occur, whereby the degree of difficulty in technology rises. In the case of a configuration in which the rotation frequency of the rollers 22, 24, 26 and 28 other than the first roller 20 are raised higher than the rotation frequency of the first roller 20, when the rotation frequency of the first roller 20 is made higher, technical problems will occur in the other rollers 22, 24, 26 and 28 that rotate at the rotation frequency higher than that of the first roller 20; hence, the rotation frequency of the first roller 20 is limited to a rotation frequency that is lower than the upper limit rotation frequency at which technical problems do not occur in the other rollers 22, 24, 26 and 28. On the other hand, in the case of a configuration in which the first to fifth rollers 20, 22, 24, 26 and 28 are rotated at the same rotation frequency, the rotation frequency of the first roller 20 can be made higher to the rotation frequency coincident with the upper limit rotation frequency of the other rollers 22, 24, 26 and 28. Hence, the rotation frequency of the first roller 20 is made higher easily. As the rotation frequency of the first roller 20 is made higher, the composite sheet 6 can be manufactured at higher speed.

Hence, it is easy to manufacture the composite sheet 6 at higher speed.

Furthermore, as the relative rotation error between the first roller 20 and the other rollers 22, 24, 26 and 28 becomes larger, the quality of the composite sheet 6 will be degraded, for example, due to the displacement of shaping and bonding positions. In the case that the first roller 20 and the other rollers 22, 24, 26 and 28 are rotated and driven separately and controlled so as to be synchronized mutually, if the rotation frequency is made higher, the relative rotation error between the first roller 20 and the other rollers 22, 24, 26 and 28 becomes larger, for example, due to delay in control, whereby it becomes difficult to maintain the quality of the composite sheet 6. On the other hand, in the case that the first roller 20 and the other rollers 22, 24, 26 and 28 are joined mutually via the gears 30, 32, 34, 36 and 38, since the relative rotation error between the first roller 20 and the other rollers 22, 24, 26 and 28 is unchanged even when the rotation frequency is changed, whereby the quality of the composite sheet 6 can be maintained even when the rotation frequency of the first roller 20 is made higher.

Moreover, since the first roller 20 and the third and fifth rollers 24 and 28 that hold the first and second sheets 2 and 4 therebetween so as to bond the sheets are equal in outer diameter, rotate at the same rotation frequency and are always opposed mutually at the same portions, the rollers fit easily. Hence, the satisfactory bonding state between the first sheet 2 and the second sheet 4 can be maintained.

What's more, each of the recessed areas 20*a* of the first roller 20 corresponds one-to-one to each of the first projections 22*a* of the second roller 22 and each of the second projections 26*a* of the fourth roller 26, the first and second projections 20*a* and 26*a* being inserted into the recessed areas 20*a*. Hence, the satisfactorily shaped states of the first and second sheets 2 and 4 can be maintained.

Still further, since the first to fifth rollers 20, 22, 24, 26 and 28 are equal in outer diameter and since the first roller 20 is opposed mutually to the second to fifth rollers 22, 24, 26 and 28 at the same portions at all times, readjustment at the time of component exchange is made easy, and assembling accuracy is maintained easily. As a result, the quality of the manufactured composite sheet 6 can be maintained constant.

Hence, even when the composite sheet 6 is manufactured at higher speed, it is possible to manufacture the composite sheet 6 having stable quality.

Next, a modification of Embodiment 1 will be described.

Modification 1

Modification 1 is configured such that the fourth roller 26 and the fifth roller 28 in the configuration of Embodiment 1 are eliminated. The second roller 22 and the third roller 24 may merely be disposed at appropriate angles around the first roller 20.

In this case, the fifth to seventh steps in the above-mentioned processing for manufacturing the composite sheet are not required.

As in the case of Embodiment 1, in Modification 1, the composite sheet can be manufactured easily at higher speed, and even when the composite sheet is manufactured at higher speed, the composite sheet having stable quality can be manufactured.

Embodiment 2

A manufacturing device and a manufacturing method for manufacturing a composite sheet according to Embodiment 2 will be described referring to FIGS. 5 and 6. Embodiment 2 is different from Embodiment 1 in that the outer diameters of the second and fourth rollers are different from the outer diameter of the first roller. In the following description, attention is paid to the differences from Embodiment 1, and the same components as those in Embodiment 1 are designated by the same reference numerals and signs.

Figure 5:
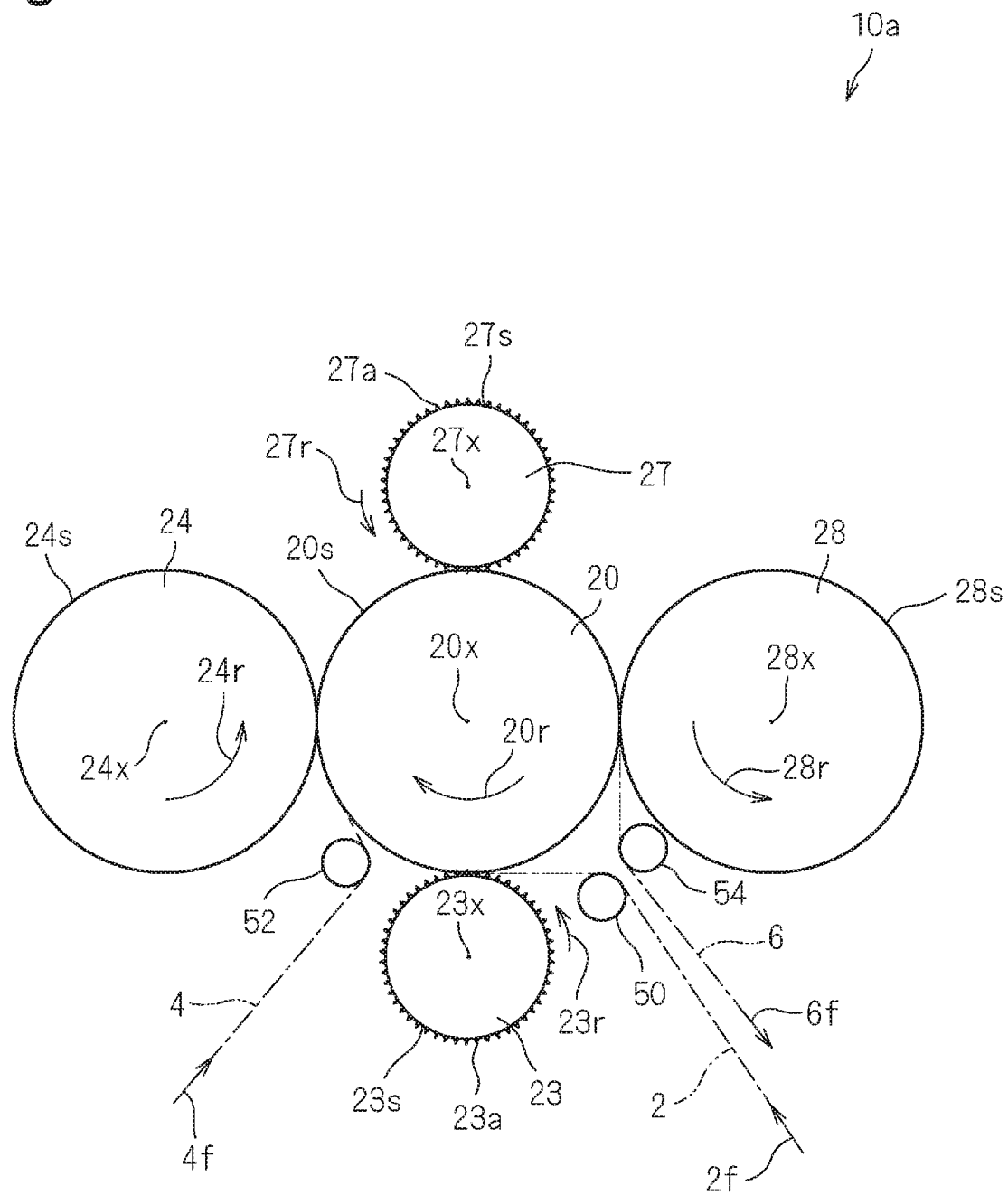
FIG. 5 is a schematic view showing a composite sheet manufacturing device (Embodiment 2)

FIG. 5 is a schematic view showing a configuration of a composite sheet manufacturing device 10*a*. As shown in FIG. 5, as in the case of the composite sheet manufacturing device 10 according to Embodiment 1, in the composite sheet manufacturing device 10*a*, second to fifth rollers 23, 24, 27 and 28 are disposed in this order so as to be adjacent to the first roller 20. The rotation center lines 20*x*, 23*x*, 24*x*, 27*x* and 28*x* of the first to fifth rollers 20, 23, 24, 27 and 28 are parallel to one another, and the first to fifth rollers 20, 23, 24, 27 and 28 rotate in the directions indicated by arrows 20*r*, 23*r*, 24*r*, 27*r* and 28*r*, respectively, in synchronization with one another. As indicated by arrows 2*f* and 4*f*, the first and second sheets 2 and 4 are fed via the first and second guide rollers 50 and 52 and conveyed through a predetermined path along the outer circumferential face 20*s* of the first roller 20 in synchronization with the rotation of the first roller 20, and then shaped into a predetermined shape by the first and second projections 23*a* and 27*a* protruding from the second and fourth outer circumferential faces 23*s*, 27*s* of the second and fourth rollers 23 and 27 and bonded to each other. The completed composite sheet 6 is ejected via the third guide roller 54 as indicated by an arrow 6*f*.

The outer diameters of the third and fifth rollers are equal to the outer diameter of the first roller 20. Unlike the case of Embodiment 1, the outer diameters of the second and fourth rollers 23 and 27 are different from the outer diameter of the first roller 20 and are preferably smaller than the outer diameter of the first roller 20. For example, the outer diameters of the second and fourth rollers 23 and 27 are approximately ⅓ of the outer diameter of the first roller 20.

Figure 6:
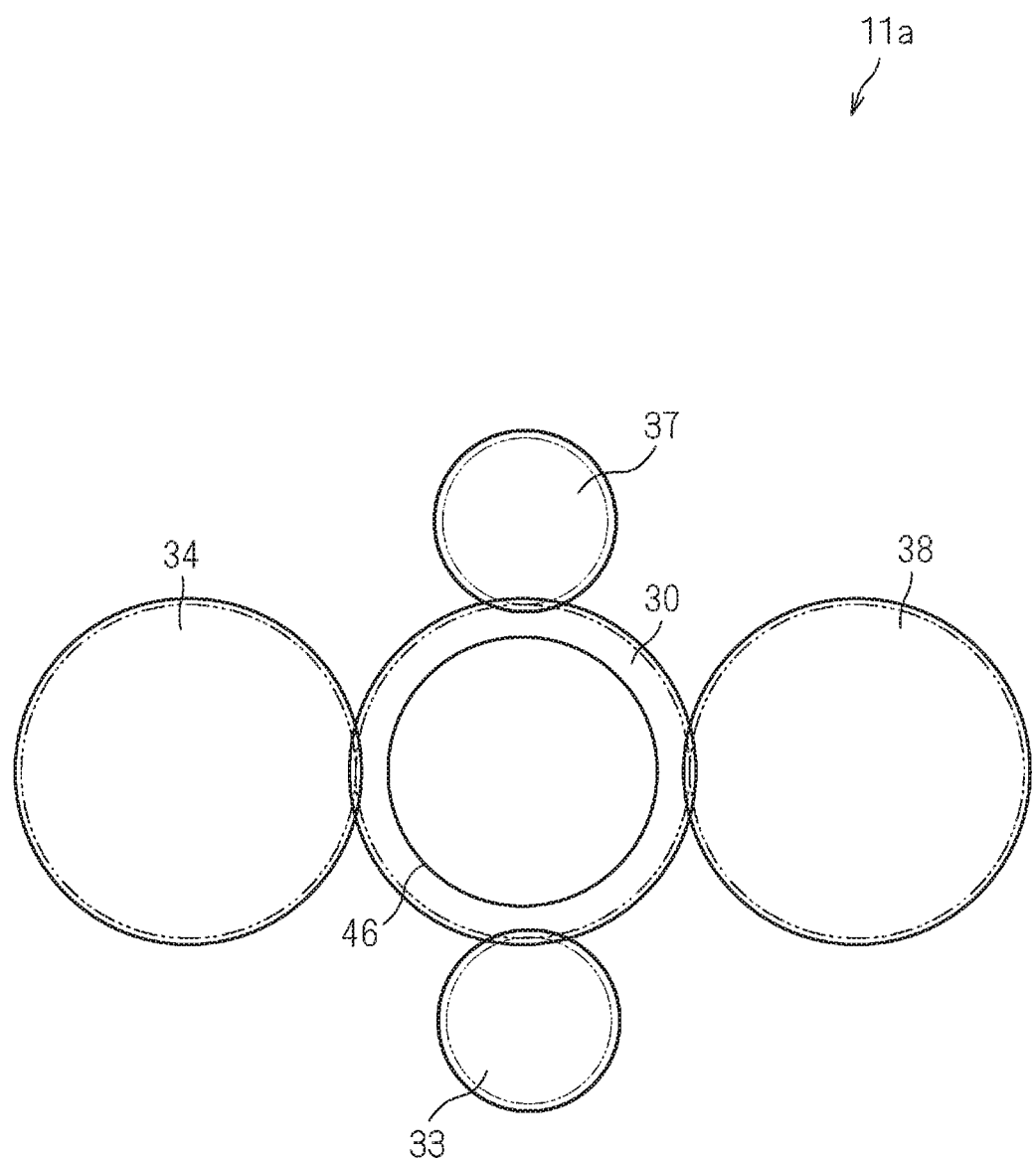
FIG. 6 is a schematic view showing the drive mechanism of the composite sheet manufacturing device (Embodiment 2)
Figure 7:
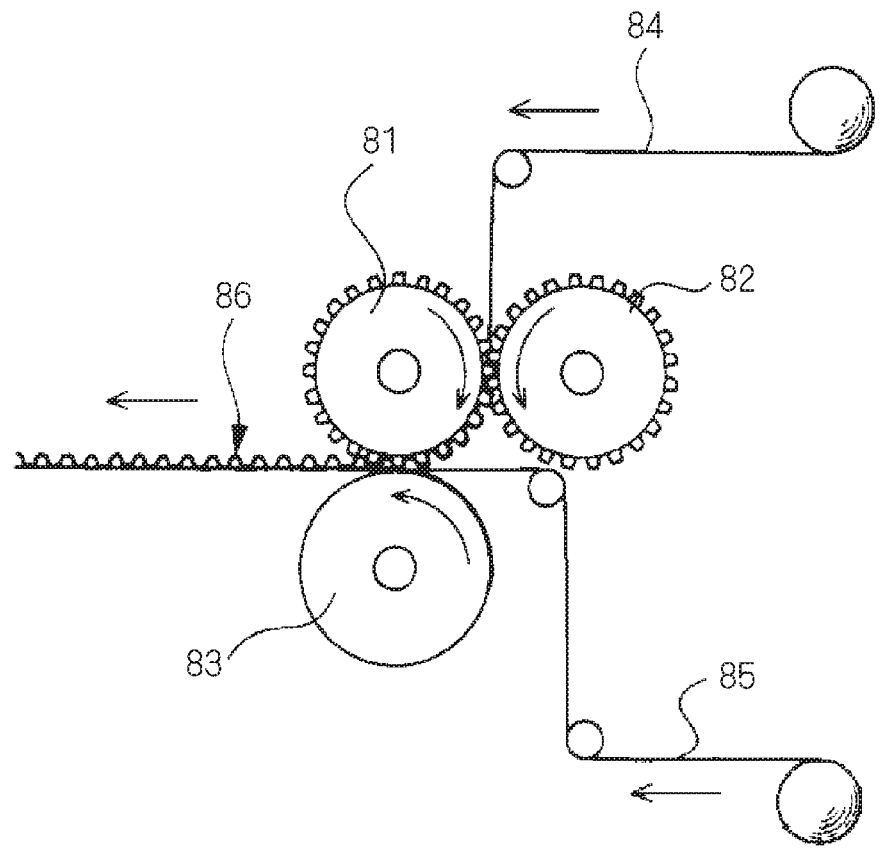
FIG. 7 is a schematic view showing a composite sheet manufacturing device (Conventional Example 1)

FIG. 6 is a schematic view showing the drive mechanism 11a of the composite sheet manufacturing device 10a, viewed in parallel to the rotation center lines 20x, 23x, 24x, 27x and 28x (see FIG. 5). As shown in FIG. 6, as in the case of the drive mechanism 11 according to Embodiment 1, in the drive mechanism 11a, second to fifth gears 33, 34, 37 and 38 are disposed around the first gear 30 so as to be engaged with the first gear 30. The mechanism is configured so that the rotations of the first to fifth gears 30, 33, 34, 37 and 38 are transmitted to the first to fifth rollers 20, 23, 24, 27 and 28, respectively. The numbers of the teeth of the first, third and fifth gears 30, 34 and 38 are the same. The numbers of the teeth of the second and fourth gears 33 and 37 are different from the number of the teeth of the first roller 20 and are preferably less than the number of the teeth of the first gear 30.

Instead of the second and fourth gears 33 and 37, timing belts or the like may be used. Furthermore, the second and fourth rollers 23 and 27 and the first, third and fifth rollers 20, 24 and 28 may be driven separately.

Next, processing for manufacturing the composite sheet 6 using the composite sheet manufacturing device 10a will be described.

(1-1) First, the second roller 23 having the first projections 23a and the third roller 24 are disposed so as to be adjacent to the first roller 20 having the multiple recessed areas 20a formed on the outer circumferential face 20s thereof, the first roller 20, the second roller 23 and the third roller 24 are rotated in synchronization with one another, and the first projections 23a of the second roller 23 are inserted into and extracted from the recessed areas 20a of the first roller 20 in a state in which a clearance is provided between each projection thereof and each recessed area 20a of the first roller 20. The outer diameters of the first roller 20 and the third roller 24 are made equal, and the third roller 24 is joined to the first roller 20 with the first gear pair composed of the gears 30 and 34, whereby the third roller 24 is rotated at the same rotation frequency as that of the first roller 20. The processing up to this step is a first step.

(1-2) Furthermore, the fourth roller 27 having the second projection 27a and the fifth roller 28 are disposed so as to be adjacent to the first roller 20, the fourth roller 27 and the fifth roller 28 are rotated in synchronization with the first roller 20, and the projections 27a of the fourth roller 27 are inserted into and extracted from the recessed areas 20a of the first projections 22a in a state in which a clearance is provided between each projection thereof and each recessed area 20a of the first roller 20. The outer diameter of the fifth roller 28 is made equal to the outer diameters of the first roller 20 and the third roller 24, the fifth roller 28 is joined to the first roller 20 with the third gear pair composed of the gears 30 and 38, and the fifth roller 28 is rotated at the same rotation frequency as that of the first roller 20. The processing up to this step is a second step.

(2) Next, the first sheet 2 is fed in between the first roller 20 and the second roller 22 that are rotating, conveyed while being supported by the outer circumferential face 20s of the first roller 20, and then passed through the space between the first roller 20 and the third roller 24. When the first sheet 2 is passed through the space between the first roller 20 and the third roller 23, the first sheet 2 is shaped by being pushed into the recessed areas 20a of the first roller 20 by the first projections 23a of the second roller 23. The processing up to this step is a second step.

(3) Next, the second sheet 4 is superimposed onto the first sheet 2 having been shaped, conveyed together with the first sheet 2, and passed through the space between the first roller 20 and the third roller 24. When the first sheet 2 and the second sheet 4 are passed through the space between the first roller 20 and the third roller 24, the first sheet 2 and the second sheet 4 are held between the first roller 20 and the third roller 24, whereby the first sheet 2 and the second sheet 4 are bonded to each other. The processing up to this step is a third step.

(4) Next, the first sheet 2 and the second sheet 4 having been passed through the space between the first roller 20 and the third roller 24 and bonded to each other are conveyed while being supported by the outer circumferential face 20s of the first roller 20, are passed through the space between the first roller 20 and the fourth roller 27. The processing up to this step is a fourth step.

(5) Next, when the first sheet 2 and the second sheet 4 are being passed through the space between the first roller 20 and the fourth roller 27, the second sheet 4 is shaped by being pushed into the recessed areas 20a of the first roller 20 by the second projections 27a of the fourth roller 27. The processing up to this step is a fifth step.

(6) Next, when the first sheet 2 and the second sheet 4 are passed through the space between the first roller 20 and the fifth roller 28, the first sheet 2 and the second sheet 4 are held between the first roller 20 and the fifth roller 28, whereby the mutual bonding of the first sheet 2 and the second sheet 4 is strengthened. The processing up to this step is a sixth step.

The composite sheet 6 can be manufactured by performing the above-mentioned steps (1) to (6).

As described above, in the composite sheet manufacturing device 10a, the first, third and fifth rollers 20, 24 and 28 being equal in outer diameter are rotated at the same rotation frequency via the first, third and fifth gears 30, 34 and 38. The composite sheet 6 can be manufactured easily at higher speed and the composite sheet 6 having stable quality can be maintained even when the composite sheet 6 is manufactured at higher speed by using the composite sheet manufacturing device 10a.

More specifically, as described above, when the rotation frequency of the rollers become higher, problems such as the heat generation of the bearings and the vibration of the rollers will occur, whereby the degree of difficulty in technology rises. In the case of a configuration in which the rotation frequency of the rollers 23, 24, 27 and 28 other than the first roller 20 are raised higher than the rotation frequency of the first roller 20, when the rotation frequency of the first roller 20 is made higher, technical problems will occur in the other rollers 23, 24, 27 and 28 that rotate at the rotation frequency higher than that of the first roller 20; hence, the rotation frequency of the first roller 20 is limited to a rotation frequency lower than the upper limit rotation frequency at which technical problems do not occur in the other rollers 23, 24, 27 and 28.

The sheets 2 and 4 are held between the first roller 20 and each of the third roller 23 and the fifth roller 28; however, since the projections 23a and 27a of the second and fourth rollers 23 and 27 are inserted into and extracted from the recessed areas 20a of the first roller 20 in a state in which a clearance is provided between each projection thereof and each recessed area 20a of the first roller 20; hence, the upper limit rotation frequency of the third and fifth rollers 24 and 28 is lower than the upper limit rotation frequency of the second and fourth rollers 23 and 27. Hence, in comparison with the conventional configuration in which the rotation frequency of the first roller is higher than the rotation frequency of the other rollers, the rotation frequency of the first roller can be made higher than that in the conventional configuration by simply making the rotation frequency of the third and fifth rollers 24 and 28 equal to the rotation frequency of the first roller 20.

Hence, the composite sheet 6 is manufactured easily at higher speed.

Since the rotation frequency of the second and fourth rollers 23 and 27 can be made higher than the rotation frequency of the first roller 20, the second and fourth rollers 23 and 27 and the gears 33 and 37 for transmitting the rotation to the second and fourth rollers 23 and 27 can be made smaller. Hence, the composite sheet manufacturing device 10*a* can be made smaller than the composite sheet manufacturing device 10 according to Embodiment 1 in size.

Furthermore, as the relative rotation error between the first roller 20 and the other rollers 23, 24, 27 and 28 becomes larger, the quality of the composite sheet 6 will be degraded, for example, due to the displacement of shaping and bonding positions. In the case that the first roller 20 and the other rollers 23, 24, 27 and 28 are rotated and driven separately and controlled so as to be synchronized mutually, if the rotation frequency is made higher, the relative rotation error between the first roller 20 and the other rollers 23, 24, 27 and 28 becomes larger, for example, due to delay in control, whereby it becomes difficult to maintain the quality of the composite sheet 6. On the other hand, in the case that the first roller 20 and the other rollers 23, 24, 27 and 28 are joined mutually via the gears 30, 33, 34, 37 and 38, since the relative rotation error between the first roller 20 and the other rollers 23, 24, 27 and 28 is unchanged even when the rotation frequency is changed, whereby the quality of the composite sheet 6 can be maintained even when the rotation frequency of the first roller 20 is made higher.

Moreover, since the first roller 20 and the third and fifth rollers 24 and 28 that hold the first and second sheets 2 and 4 therebetween so as to bond the sheets are equal in outer diameter, rotate at the same rotation frequency, and are always opposed mutually at the same portions, the rollers fit easily. Hence, the satisfactory bonding state between the first sheet 2 and the second sheet 4 can be maintained.

Still further, since the first, third and fifth rollers 20, 24 and 28 are equal in outer diameter and since the first roller 20 is opposed mutually to the third and fifth rollers 24 and 28 at the same portions at all times, readjustment at the time of component exchange is made easy, and assembling accuracy is maintained easily. As a result, the quality of the manufactured composite sheet 6 can be maintained constant.

Hence, even when the composite sheet 6 is manufactured at higher speed, it is possible to manufacture the composite sheet 6 having stable quality.

Next, a modification of Embodiment 2 will be described.

Modification 2

Modification 2 is configured such that the fourth roller 27 and the fifth roller 28 in the configuration of Embodiment 2 are eliminated. The second roller 23 and the third roller 24 may merely be disposed at appropriate angles around the first roller 20.

In this case, the fifth to seventh steps in the above-mentioned processing for manufacturing the composite sheet are not required.

As in the case of Embodiment 2, in Modification 2, the composite sheet can be manufactured easily at higher speed, and even when the composite sheet is manufactured at higher speed, the composite sheet having stable quality can be manufactured.

CONCLUSION

With the composite sheet manufacturing device and manufacturing method described above, the composite sheet can be manufactured easily at higher speed, and even when the composite sheet is manufactured at higher speed, the composite sheet having stable quality can be manufactured.

The present invention is not limited to the above-mentioned embodiments and can be modified variously and embodied.

DESCRIPTION OF REFERENCE NUMERALS

2 first sheet
4 second sheet
6 composite sheet
10 composite sheet manufacturing device
20 first roller
20*a* recessed area
20*s* first outer circumferential face
22, 23 second roller
22*a*, 23*a* first projection
22*s*, 23*s* second outer circumferential face
24 third roller
24*s* third outer circumferential face
26, 27 fourth roller
26*a*, 27*a* second projection
26*s*, 27*s* fourth outer circumferential face
28 fifth roller
28*s* fifth outer circumferential face
30, 32, 33, 34, 36, 37, 38 gear

The invention claimed is:
1. A composite sheet manufacturing device comprising:
a first roller having a first outer circumferential face, a plurality of recessed areas retracted from the first outer circumferential face, and a first gear on an axis thereof,
a second roller disposed so as to be adjacent to the first roller, rotated in synchronization with the first roller, and having a second outer circumferential face opposed to the first outer circumferential face of the first roller, a plurality of first projections that protrude from the second outer circumferential face so as to be inserted into and extracted from the recessed areas of the first roller in a state in which a clearance is provided between each first projection thereof and each recessed area of the first roller, and a second gear on an axis thereof directly engaging the first gear,
a third roller disposed so as to be adjacent to the first roller, rotated in synchronization with the first roller, and having a third outer circumferential face opposed to the first outer circumferential face of the first roller, and a third gear on an axis thereof directly engaging the first gear,
a fourth roller disposed so as to be adjacent to the first roller, rotated in synchronization with the first roller, and having a fourth outer circumferential face opposed to the first outer circumferential face of the first roller, a plurality of second projections that protrude from the fourth outer circumferential face so as to be inserted into and extracted from the recessed areas of the first roller in a state in which a clearance is provided between each second projection thereof and each recessed area of the first roller, and a fourth gear on an axis thereof directly engaging the first gear, and a fifth roller disposed so as to be adjacent to the first roller, rotated in synchronization with the first roller, and having a fifth outer circumferential face opposed to the first outer circumferential face, and a fifth gear on an axis thereof directly engaging the first gear, wherein a first sheet is fed in between the first roller and the second roller, conveyed while being supported by the first outer circumferential face of the first roller and passed through a space between the first roller and the second roller, so that when the first sheet is passed through the space between the first roller and the second roller, the first projections of the second roller push the first sheet into the recessed areas of the first roller, and thereby the first sheet is shaped, a second sheet is superimposed onto the shaped first sheet and conveyed together with the first sheet and then passed through a space between the first roller and the third roller, so that when the first sheet and the second sheet are passed through the space between the first roller and the third roller, the first roller and the third roller hold the first sheet and the second sheet therebetween, and thereby the first sheet and the second sheet are bonded to each other, each outer diameter of the first roller, the third roller and the fifth roller has a same size, each outer diameter of a first tip circle of the first projections that protrude from the second outer circumferential face of the second roller and a second tip circle of the second projections that protrude from the fourth outer circumferential face of the fourth roller has a same size, and numbers of teeth of each of the first gear, third gear and fifth gear are the same, and numbers of teeth of each of the second and fourth gears are the same.

2. The composite sheet manufacturing device according to claim 1, wherein each of the outer diameters of the first tip circle and the second tip circle is smaller than the outer diameter of each of the first roller, the third roller and the fifth roller, and a rotational frequency of each of the first tip circle and the second tip circle is higher than a rotational frequency of the first roller.

3. The composite sheet manufacturing device according to claim 2, wherein the first sheet and the second sheet having been passed through the space between the first roller and the third roller and bonded to each other are conveyed while being supported by the first outer circumferential face of the first roller and are passed through a space between the first roller and the fourth roller and then passed through a space between the first roller and the fifth roller, when the first sheet and the second sheet are passed through the space between the first roller and the fourth roller, the second projections of the fourth roller push the second sheet into the recessed areas of the first roller, and thereby the second sheet is shaped, and when the first sheet and the second sheet are passed through the space between the first roller and the fifth roller, the first roller and the fifth roller hold the first sheet and the second sheet therebetween, and thereby the mutual bonding of the first sheet and the second sheet is strengthened.

4. The composite sheet manufacturing device according to claim 1, wherein the outer diameter and a rotational speed of each of the first tip circle and the second tip circle are equal to the outer diameter and a rotational speed of each of the first roller, the third roller and the fifth roller.

5. The composite sheet manufacturing device according to claim 1, wherein the first outer circumferential face and the recessed areas of the first roller are configured to suction-hold the first sheet.

6. The composite sheet manufacturing device according to claim 5, wherein each of the first roller, and/or the third roller and the fifth roller has a heater therein so that when the first sheet and the second sheet are held between the first roller and the third roller, the first sheet and the second sheet are bonded to each other by thermal fusion, and when the first sheet and the second sheet having been bonded to each other are held between seal projections of the first roller and the fifth outer circumferential face of the fifth roller, mutual bonding is strengthened.

7. The composite sheet manufacturing device according to claim 1, wherein the first roller includes seal projections on the first outer circumferential face where the first sheet and the second sheet contacting with each other are bonded intermittently.

* * * * *